(12) United States Patent
Emmerich et al.

(10) Patent No.: US 11,146,723 B2
(45) Date of Patent: Oct. 12, 2021

(54) OPTICAL SCOPE SYSTEM FOR CAPTURING AN IMAGE OF A SCENE

(71) Applicant: Sony Corporation, Tokyo (JP)

(72) Inventors: Thimo Emmerich, Stuttgart (DE); Zoltan Facius, Stuttgart (DE); Paul Springer, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/464,688

(22) PCT Filed: Dec. 14, 2017

(86) PCT No.: PCT/EP2017/082891
§ 371 (c)(1),
(2) Date: May 29, 2019

(87) PCT Pub. No.: WO2018/109109
PCT Pub. Date: Jun. 21, 2018

(65) Prior Publication Data
US 2019/0327421 A1    Oct. 24, 2019

(30) Foreign Application Priority Data
Dec. 16, 2016   (EP) .................................... 16204872

(51) Int. Cl.
*H04N 5/232*    (2006.01)
*A61B 1/00*     (2006.01)
(Continued)

(52) U.S. Cl.
CPC ... *H04N 5/232125* (2018.08); *A61B 1/00188* (2013.01); *A61B 1/045* (2013.01);
(Continued)

(58) Field of Classification Search
CPC ............ H04N 5/2254; H04N 5/23232; H04N 5/232125; H04N 5/23216; H04N 9/097;
(Continued)

(56) References Cited

U.S. PATENT DOCUMENTS 5,908,391 A    6/1999   Muzilla et al.
6,322,496 B1   11/2001  Iida et al.
(Continued)

FOREIGN PATENT DOCUMENTS

EP             3072437 A1    9/2016

OTHER PUBLICATIONS

International Search Report dated Feb. 22, 2018 for PCT/EP2017/082891 filed on Dec. 14, 2017, 11 pages.
(Continued)

*Primary Examiner* — Daniel G Mariam
(74) *Attorney, Agent, or Firm* — Xsensus LLP

(57) ABSTRACT

An optical device for capturing an image of a scene, the optical device comprising: a plurality of image sensors each operable to capture a respective initial image of the scene; a lens arrangement operable to receive light from the scene and to form each initial image on each respective image sensor, each image sensor being located at a different respective distance from the lens arrangement; and an image processor operable to generate the captured image of the scene on the basis of image data from one or more of the captured initial images.

13 Claims, 4 Drawing Sheets

(51) Int. Cl.
*A61B 1/045* (2006.01)
*H04N 5/225* (2006.01)
*H04N 9/097* (2006.01)

(52) U.S. Cl.
CPC ....... *H04N 5/2254* (2013.01); *H04N 5/23216* (2013.01); *H04N 5/23232* (2013.01); *H04N 5/232133* (2018.08); *H04N 9/097* (2013.01); *H04N 2005/2255* (2013.01)

(58) Field of Classification Search
CPC ........ H04N 2005/2255; A61B 1/00188; A61B 1/045
USPC ......................................................... 382/128
See application file for complete search history.

(56) References Cited

U.S. PATENT DOCUMENTS

| | | | | |
|---|---|---|---|---|
| 10,324,300 | B2* | 6/2019 | Duckett | ............... H05K 5/0021 |
| 10,571,679 | B2* | 2/2020 | Duckett, III | ......... H04N 5/2258 |
| 2004/0125228 | A1 | 7/2004 | Dougherty | |
| 2005/0143624 | A1* | 6/2005 | Iddan | ................. A61B 1/00094 600/112 |
| 2013/0038689 | A1 | 2/2013 | McDowall | |
| 2013/0041221 | A1 | 2/2013 | McDowall et al. | |
| 2013/0286176 | A1 | 10/2013 | Westwick et al. | |
| 2014/0031802 | A1 | 1/2014 | Melsky et al. | |
| 2016/0286187 | A1* | 9/2016 | Takenaga | ........... A61B 1/00186 |
| 2016/0309141 | A1* | 10/2016 | Pulli | .................... H04N 5/2226 |
| 2016/0360091 | A1 | 12/2016 | Lindskog et al. | |

OTHER PUBLICATIONS

Guichard et al., "Extended Depth-of-Field using sharpness transport across Color Channels" vol. 7250, XP002676338, Jan. 1, 2009, 12 pages.
Hariharan, "Extending Depth of Field via Multifocus Fusion", University of Tennessee, Dec. 2011, pp. 1-157.

* cited by examiner

OPTICAL SCOPE SYSTEM FOR CAPTURING AN IMAGE OF A SCENE

CROSS-REFERENCE TO RELATED APPLICATIONS

The present application is based on PCT filing PCT/EP2017/082891, filed Dec. 14, 2017 which claims priority to EP 16204872.2, filed Dec. 16, 2016, the entire contents of each are incorporated herein by reference.

BACKGROUND

Field of the Disclosure

The present disclosure relates to a capturing an image of a scene. In particular, the present disclosure relates to capturing an image in an optical scope system.

Description of the Related Art

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

A problem with certain image capture devices such as those used in industrial instruments (such as industrial endoscopes) or medical instruments (such as medical endoscopes) is the limited depth of field at which high spatial frequencies can be obtained in order to capture a sufficiently sharp image. In order to improve the depth of field, the size of the aperture through which light travels to form the image to be captured can be reduced (increasing the so-called F number (F#) of the image capture device). This leads to a larger depth of field, but, in turn, reduces the resolution/in-focus sharpness (due to diffraction) and increases the noise of the captured image (due to there being less received light and thus a reduced signal to noise ratio). In other words, there is a trade off between having a larger depth of field and having greater in-focus sharpness and low noise images.

Furthermore, as the form factor of such image capture devices is reduced (for example, to allow smaller form factor endoscopes), thus requiring image capture sensors with smaller pixel sizes, the problems of this approach are set to get worse.

Moreover, in many endoscope applications such as surgical endoscopy or industrial endoscopy, high resolution images such as 4K, 8K or the like are also desired. This means that the imager becomes larger and so there is a trade-off required between the size of imager and the depth of focus, In other words, a problem exists of how to provide an extended depth of field when high resolution images (such as those provided using larger imagers) are required.

It is an aim of the present disclosure to address at least one of these problems.

SUMMARY

The present technique provides an optical scope system for capturing an image of a scene, the optical device comprising: a plurality of image sensors each operable to capture a respective initial image of the scene; a lens arrangement operable to receive light from the scene and to form each initial image on each respective image sensor, each image sensor being located at a different respective distance from the lens arrangement; and an image processor operable to generate the captured image of the scene on the basis of image data from one or more of the captured initial images.

This arrangement is advantageous because an image is produced that has an improved depth of field for a given resolution/in-focus sharpness of image.

The present technique also provides a method of capturing an image of a scene, the method comprising: capturing a plurality of initial images of the scene, each initial image of the scene being captured using a respective one of a plurality of image sensors, wherein each image sensor is located at a different respective distance from a lens arrangement operable to receive light from the scene and to form each initial image on each respective image sensor; and generating the captured image of the scene on the basis of image data from one or more of the captured initial images.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1A:
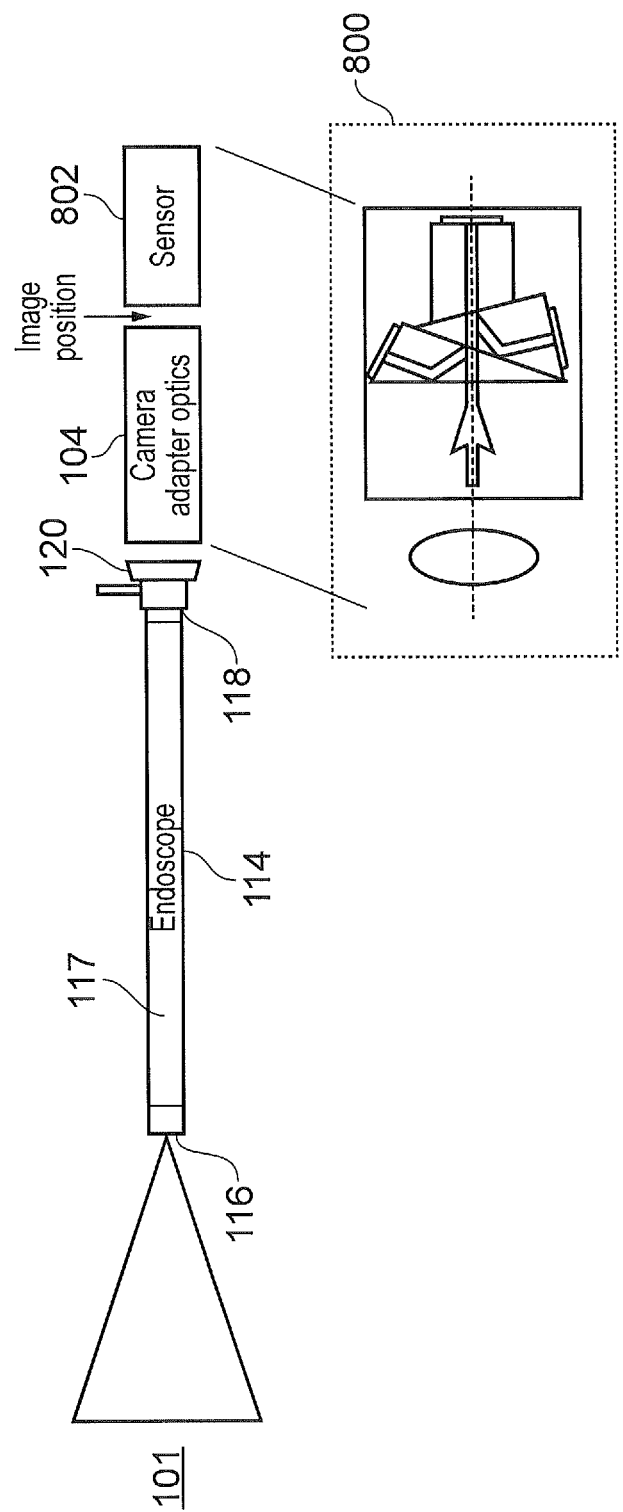
FIGS. 1A and 1B show an optical scope system according to an embodiment of the present technique.

Referring now to the drawings, wherein like reference numerals designate identical or corresponding parts throughout the several views.

Figure 1B:
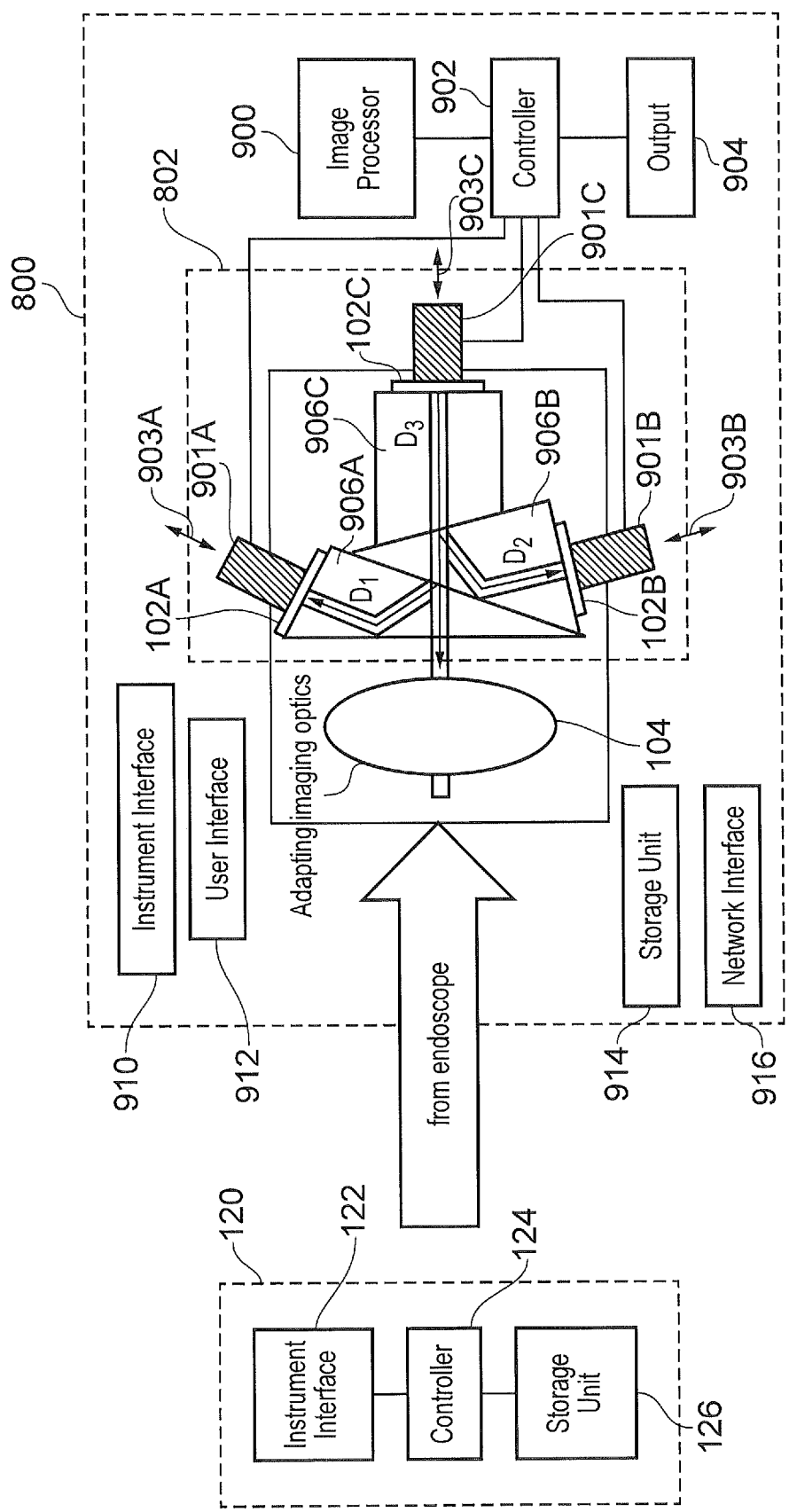

FIGS. 1A and 1B show an endoscope system 800 for capturing an image of the scene 101 according to an embodiment of the present technique. The endoscope system 800 is an example of an optical scope system and comprises an image sensor 802, a lens arrangement 104 (this being an arrangement of one or more lenses and being camera adapter optics, also known as adapting imaging optics, in this embodiment), an image processor 900 and an output unit 904. The operation of each of the image processor 900 and output unit 904 is controlled by a controller 902. The image sensor 802 and the lens arrangement 104 may form part of a camera head and the image processor 900 and the output unit 904 may form part of a camera control unit.

In operation, the lens arrangement 104 receives light from the scene and forms a plurality of initial images of the scene at the image sensor 802 using the received light. The image sensor 802 then captures each initial image of the scene (that is, it captures each initial image of the scene as an electronic image). These electronic images are then processed by the image processor 900 so as to form a final image of the scene on the basis of image data from one or more of the captured initial images. The final image of the scene is then output for display and/or storage by the output unit 904.

In this particular embodiment, the light from the scene used to form the captured image is received from a medical instrument (in this example, a medical endoscope 114, such as a surgical endoscope). That is, the lens arrangement 104 receives light from the scene captured by the medical instrument and forms the initial images of the scene at the image sensor using this received light. It will be appreciated, however, that light from the scene may be received from any other type of instrument, as long as the light is focused by the lens arrangement 104 at the image sensor 802. An example of another type of instrument is an industrial instrument such as an industrial endoscope. In the example of FIG. 1A, the instrument is a medical endoscope 114. Light from the scene enters an entrance pupil at a distal end 116 of the medical endoscope, travels down one or more optical fibres 117 of the endoscope, and exits the endoscope through an exit pupil at the proximal end 118 of the endoscope. This light is then received by the lens arrangement 104 and a plurality of initial images are formed at the image sensor 802.

The image sensor 802 of the endoscope system 800 comprises a plurality of image sensors 102A, 102B and 102C (each image sensor being a charged coupled device (CCD), complementary metal oxide semiconductor (CMOS) or Organic CMOS image sensor, for example). Each of the plurality of image sensors is operable to capture a respective one of the initial images of the scene. That is, the lens arrangement 104 operable to receive light from the scene and to form each initial image on a respective one of the image sensors 102A, 102B and 102C. Each image sensor is located at a different respective distance from the lens arrangement so that the in-focus position in the scene is different for each initial image. In the example of FIG. 1B, the image sensor 102A is located at a distance $D_1$ from the lens arrangement, the image sensor 102B is located at a distance $D_2$ from the lens arrangement, and the image sensor 102C is located at a distance $D_3$ from the lens arrangement, wherein $D_1 \neq D_2 \neq D_3$. This means that each object in the scene is in focus in different one of the captured initial images, depending on its object distance in the scene. In the example of FIG. 1B, each of the plurality of image sensors is located along a different respective optical path with respect to the lens arrangement. This is enabled by an arrangement of prisms 906A, 906B and 906C, which act to split beams of light received from the lens arrangement 104 along a plurality of optical paths. Each image sensor is then placed along a respective one of the optical paths at the appropriate distance from the lens arrangement. It will be appreciated that any suitable method of splitting received beams of light into a plurality of beams following different optical paths could be used in the lens 802, as will be appreciated by the skilled person.

Once each initial image has been captured, the image processor 900 determines an image sharpness level for corresponding portions of each of the captured initial images. The image processor 900 then determines the highest one of the determined image sharpness levels and generates, on the basis of image data from each of the captured initial images, the final image of the scene so that a portion of the final image of the scene corresponding to the corresponding portions of each of the captured initial images has a sharpness level equal to the determined highest image sharpness level.

Figure 2:
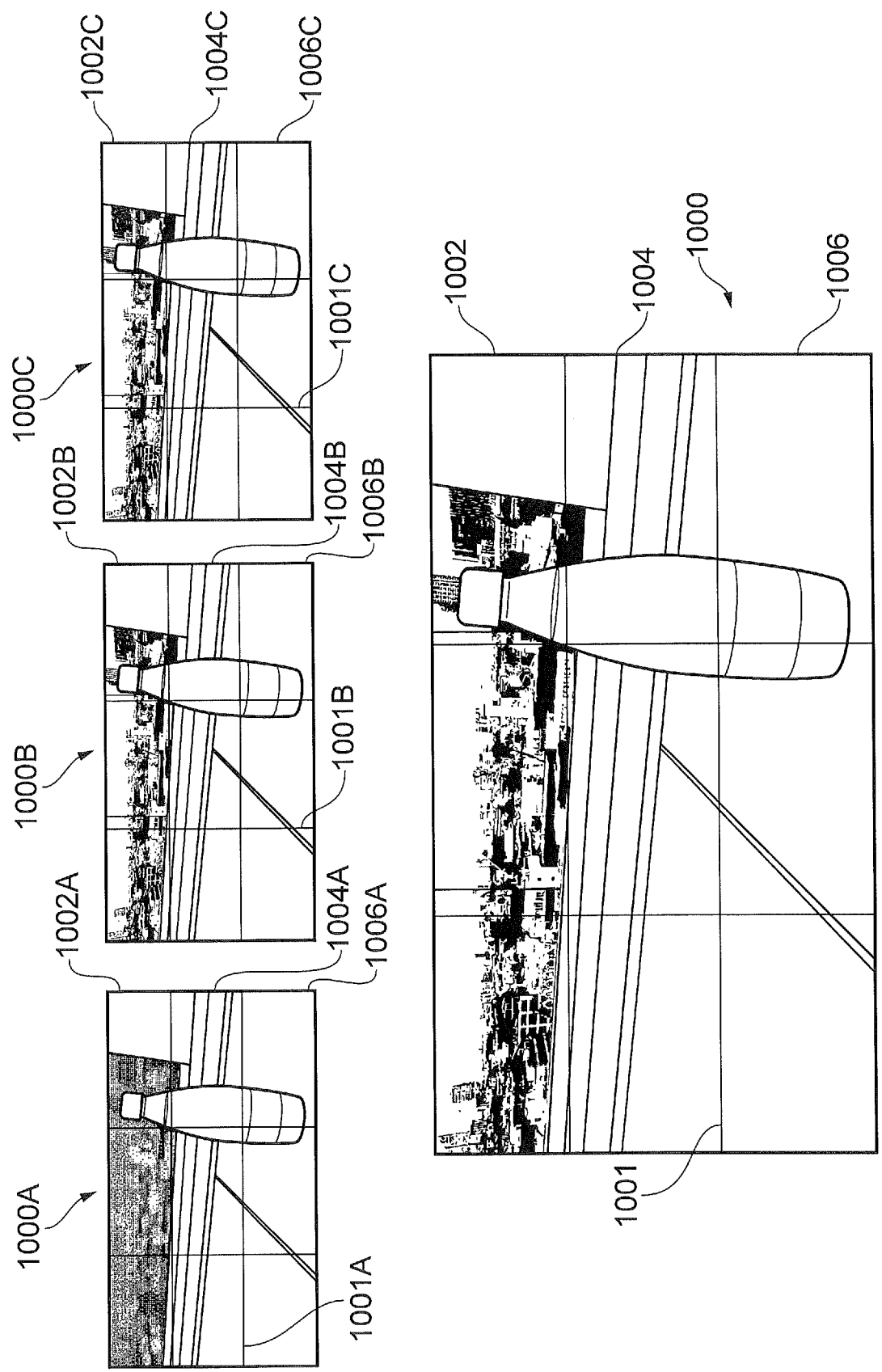
FIG. 2 shows an example associated with the optical device.

Such an arrangement is exemplified with reference to FIG. 2, in which three initial images of a scene 1000A, 1000B and 1000C are used to generate a final image of the scene 1000. It can be seen that the in-focus position of each of the initial images 1000A, 1000B and 1000C is different, as will occur when each of the initial images is captured by a different respective image sensor positioned at a different respective distance from the lens arrangement 104.

Each of the initial images and final image is divided into 9 portions as indicated by the grids 1001A, 1001B, 1001C and 1001 marked on each image. Corresponding portions of the images are those portions appearing at the same location in each image. Thus, for example, portion 1002A in image 1000A, portion 1002B in image 1000B, portion 1002C in image 1000C and portion 1002 in image 1000 are corresponding portions because each of them is the top right portion for its respective image. Similarly, portion 1006A in image 1000A, portion 1006B in image 1000B, portion 1006C in image 1000C and portion 1006 in image 1000 are corresponding portions because each of them is the bottom right portion for its respective image.

Due to the different in-focus positions of each initial image, a first object appearing to be in focus in a first portion of one of the initial images will be out of focus in the corresponding portions of the other initial images. On the other hand, a second object appearing to be out of focus in a second portion of the one of the initial images will be in focus in the corresponding portion of one of the other initial images. A final image in which both the first and second objects appear to be in focus can therefore be generated on the basis of the first portion of the initial image in which the first object appears to be in focus and on the basis of the second portion of the initial image in which the second object appears to be in focus. Using this principle, a final image in which all objects in the image (which appear to be in focus in one of the initial images) appear to be in focus may be generated by the image processor 900. It is noted that, in this description, an object which appears to be more in focus may be described as appearing sharper, where as an object which appears to be less in focus may be described as appearing less sharp.

This is exemplified in FIG. 2, in which portion 1006A of image 1000A has the sharpest overall focus (compared to portion 1006B of image 1000B and portion 1006C of image 1000C), portion 1004B of image 1000B has the sharpest focus (compared to portion 1004A of image 1000A and portion 1004C of image 1000C) and portion 1002C of image 1000C has the sharpest focus (compared to portion 1002A of image 1000A and portion 1002B of image 1000B). Portion 1006 of final image 1000 is therefore based on the image sharpness level of portion 1006A of image 1000A. Similarly, portion 1004 of final image 1000 is based on the image sharpness level of portion 1004B of image 1000B, and portion 1002 of final image 1000 is based on the image sharpness level of portion 1002C of image 1000C. Each portion of the final image 1000 is therefore generated on the basis of the corresponding portion of the one of the initial images with the highest image sharpness level for that portion. This allows the final image to have a large perceived depth of field, even though each initial image may have a shallow depth of field. A larger aperture (smaller F#) may therefore be used (thus allowing increased in-focus sharpness (resolution) of the captured image and reduced image noise) whilst the problem of reduced depth of field resulting from using a larger aperture is alleviated.

In the example of FIG. 2, each initial image is divided into only 9 portions in this example for the sake of simplicity. In reality, however, it will be appreciated that there will be a much greater number of smaller portions so that all objects within each image portion are at substantially the same object distance. This helps reduce the risk of a single image portion comprising captured objects of significantly different object distance (in this case, even the sharpest image portion may contain out of focus details, resulting in a reduction in quality of the resulting final image). It will be appreciated that the smallest size of an image portion is limited by the number of pixels of each image sensor required in order to determine sharpness information for that image portion.

This determination of sharpness levels can be performed by partial image block (comprised of a block of pixels which form a sub-region of the image) or based on pixel by pixel basis. If the system applies pixel by pixel basis transportation, the quality of image is improved on a pixel by pixel basis. However, if the system applies determining sharpness level for each sub-region, calculation cost will be reduced compared to the pixel by pixel basis In a first variant of the present technique, each of the image sensors captures light using primary colours, namely each of red, green and blue (RGB) colour channels (for example, using an RGB Bayer array). The image processor 900 then generates each portion of the final image of the scene on the basis of the one of the corresponding portions the initial images which has the highest image sharpness level. In one example, the measurement of the sharpness of each portion of each initial image occurs before demosaicing of the image. The demosaicing may then be carried out after the appropriate portions of the initial images have been combined in order to generate the final image.

In a second variant of the present technique, each of the image sensors captures light using a different respective one of red, green and blue (RGB) colour channels (so that, for example, image sensor 102A captures red light, image sensor 102B captures green light and image sensor 102C captures blue light). The image processor 900 then generates each portion of the final image of the scene by transporting the image sharpness level of the corresponding portion of the initial image with the highest measured image sharpness level to the corresponding portions of the other initial images, and combining the corresponding portion of the initial image which has the highest image sharpness level with the corresponding portions of the other initial images to which the measured highest image sharpness level has been transported.

This is advantageous because as the sharpness levels are different among RGB, this system can obtain the best sharpness values and provide this value to the other colour signals. This provides a higher quality resultant image. Also, this arrangement is easy to arrange using 3CMOS sensor systems.

As a further variant of the present technique, the system may have a plurality of image sensors (for example, more than one, two or even three). In addition to RGB colour, further sensor for infrared (IR) or Near-Infrared (NIR) wavelength may be arranged. This NIR wavelength band is useful for fluorescence biomedical imaging or imaging vessels with more perceivable colour.

It is noted that, with the above-mentioned variants, the determination of the sharpness level of each portion of the initial images may be determined using a suitable sharpness measurement technique, as is known in the art. Furthermore, the transport of a measured sharpness level of a portion of a first initial image to a corresponding portion of a second initial image may be carried out using a suitable sharpness transport technique, as is known in the art.

As shown in FIG. 1B, the image sensor 802 may comprise a plurality of image sensor adjustment devices 901A, 901B and 901C. Each image sensor adjustment device is operable to adjust the distance of a respective one of the image sensors from the lens arrangement. The controller 902 is operable to control each of the image sensor adjustment devices to adjust the distance of each respective image sensor from the lens arrangement based on the optical properties of the instrument (such as endoscope 114) via which light is received, thus helping to ensure sufficient depth of field extension for a variety of different instruments. Such an arrangement allows, for example, the distance $D_1$, $D_2$ and $D_3$ of each respective image sensor from the lens arrangement 104 to be adjusted in advance based on the optical properties of the instrument to be used so as to achieve an optimal set of distances $D_1$, $D_2$ and $D_3$. An optimal set of distances may be determined by, for example, the set of distances which maximise the depth of field of each initial image. In an embodiment, each image sensor is mounted on a respective one of the image sensor adjustment devices. Each image sensor adjustment device comprises an electro-mechanical actuator or the like (not shown) in order to adjust the position of its respective sensor. As such, the appropriate distances are adjusted depending on the types of scopes attached to the instrument interface. Hence, image quality of final image (i.e. extended depth of focus) is achieved.

The controller 902 may control the position of the image sensors to be adjusted on the basis of, for example, information received directly from the instrument (such as endoscope 114) attached to the optical device 800 via instrument interface 910 or from information received from a user of the optical device 800 via user interface 912. It is noted that the optical device 800 may have one or both of the instrument interface 910 and user interface 912.

This instrument interface arrangement is advantageous it this is used for an optical scope system, such as an endoscope system as the endoscope system is generally compatible for various types of scopes (different diameters, direct-view or oblique view endoscopes).

The instrument interface 910 may be any suitable interface via which the optical device 800 can receive information with the instrument (such as endoscope 114) to which it is attached. In one variant, the instrument (such as endoscope 114) attached to the endoscope system 800 has a corresponding instrument interface together with a suitable controller and storage unit for storing information which, when received by the controller 902, allows the controller 902 to determine the image sensor distances to be used with the instrument. Such an arrangement is exemplified in in FIGS. 1A and 1B, which shows how a coupling portion 120 of the endoscope 114 for physically coupling the endoscope 114 to the endoscope system 800 comprises an instrument interface 122, controller 124 and storage unit 126. Information on the basis of which the controller 902 can determine the image sensor distances $D_1$, $D_2$ and $D_3$ to be used with the endoscope 114 is stored in the storage unit 126. When the endoscope 114 and optical device 800 are physically coupled together, the instrument interface 122 of the endoscope and the instrument interface 910 of the optical device are in sufficient proximity for information to be exchanged between them. The controller 124 of the endoscope 114 thus controls the information stored in the storage unit 126 to be transmitted to the controller 902 of the optical device via the instrument interfaces 122 and 912. The instrument interfaces may exchange information using any suitable technique, such as via Bluetooth®, Wi-Fi® or Near Field Communication (NFC), for example, or via a suitable physical connection such as electrical contact. In an alternative variant, the instrument does not have a corresponding instrument interface, but, rather, has suitable markings which are detectable by the instrument interface 910 of the endoscope system 800. In this case, the information on the basis of which the controller 902 can determine the image sensor distances to be used with the instrument is indicated by the markings. The markings may comprise, for example, a barcode, Quick Response (QR) code or the like and the instrument interface 910 of the optical device 800 may be a barcode reader, QR code reader or other suitable reader.

The user interface 912 may be any suitable interface for allowing a user to provide information to the optical device 800 for use by the controller 902 in determining the image sensor distances to be used with the instrument. For example, the user interface 912 may comprise one or more of a touch screen, keyboard, various control buttons, a gesture recognition system, a speech recognition system, or the like.

The information provided to the controller 902 via the instrument interface 910 or user interface 912 may be any suitable information which allows the controller 902 to determine the image sensor distances to be used with the instrument. For example, the information may comprise the image sensor distances $D_1$, $D_2$ and $D_3$ themselves or may comprise one or more optical properties of the instrument so as to allow the controller 902 to calculate the image sensor distances $D_1$, $D_2$ and $D_3$. Alternatively, the information may simply identify the particular instrument (for example, via a model number or serial number of the like), and the controller 902 may then look up the instrument in a suitable database in order to obtain the image sensor distances or one or more optical properties for calculating the image sensor distances associated with that instrument. The database may be stored in a storage unit 914 of the optical device 800 in advance. Alternatively, the database may be stored at a remote location on a network (such as the internet), which the controller 902 is able to access via network interface 916. The network interface 916 may be any suitable interface such as a Wi-Fi® or Ethernet interface, for example. The database, whether stored in the storage unit 914 or at a remote location may be updatable. This allows information to be added to the database for newly available instruments which are compatible with the endoscope system 800, thus allowing suitable image sensor distances to be determined for such newly available instruments. This allows the endoscope to be changed more quickly which is important in an industrial or medical setting.

Figure 3:
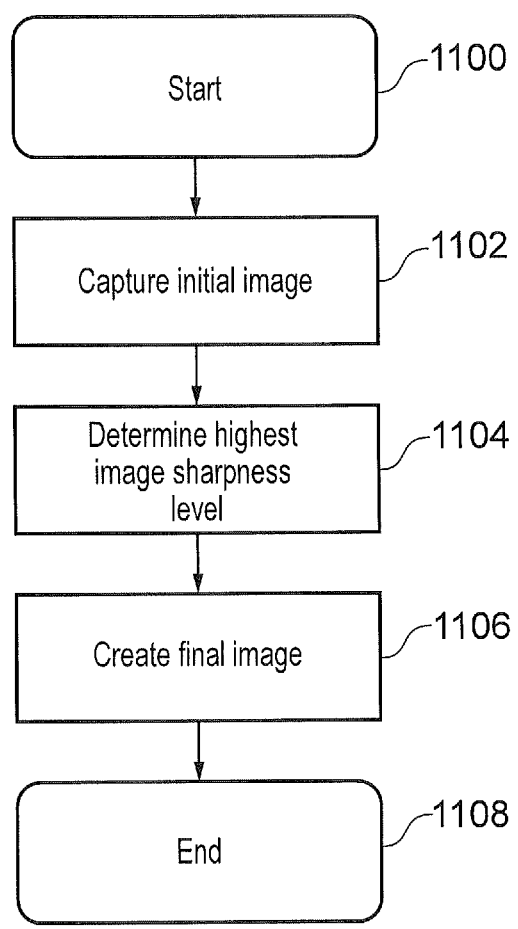
FIG. 3 shows a flow chart schematically illustrating a process according to an embodiment of the present technique.

FIG. 3 shows a flow chart schematically illustrating a process according to an embodiment of the present technique. The process starts at step 1100. At step 1102, the controller 902 controls the plurality of image sensors 102A, 102B and 102C to capture a plurality of initial images of the scene. Each initial image of the scene is captured using a respective one of the plurality of image sensors. Each image sensor is located at a different respective distance from the lens arrangement 104 operable to receive light from the scene and to form each initial image on each respective image sensor. At step 1104, the controller 902 controls the image processor 900 to determine an image sharpness level for corresponding portions of each of the captured initial images and to determining the highest one of the determined image sharpness levels. At step 1106, the controller 902 controls the image processor 900 to generate, on the basis of image data from each of the captured initial images, the captured image of the scene so that a portion of the captured image of the scene corresponding to the corresponding portions of each of the captured initial images has a sharpness level equal to the determined highest image sharpness level. The process then ends at step 1108.

Although the foregoing has described the optical device in the context of instruments (either medical or industrial, for example), the disclosure is not so limited. For example, the optical device may be used in other devices such as cameras (either still cameras or video cameras) or the like. Also the scope described here is not limited to be inserted into a body (i.e. endoscope), and can be used for microscope or exoscope or the other types of optical scope.

Various embodiments of the present disclosure are defined by the following numbered clauses:

1. An optical scope system (800) for capturing an image of a scene, the optical device comprising:
   a plurality of image sensors (102A-102C) each operable to capture a respective initial image of the scene;
   a lens arrangement (104) operable to receive light from the scene and to form each initial image on each respective image sensor, each image sensor being located at a different respective distance from the lens arrangement; and
   an image processor (900) operable to generate the captured image of the scene on the basis of image data from one or more of the captured initial images.

2. The optical scope system according to clause 1, wherein the image processor is operable to:
   determine an image sharpness level for corresponding portions of each of the captured initial images;
   determine the highest one of the determined image sharpness levels; and
   generate, on the basis of image data from each of the captured initial images, the captured image of the scene so that a portion of the captured image of the scene corresponding to the corresponding portions of each of the captured initial images has a sharpness level equal to the determined highest image sharpness level.

3. The optical scope system according to clause 2, wherein:
   each of the image sensors is operable to capture light using each of red, green and blue (RGB) colour channels; and
   the image processor is operable to generate the portion of the captured image of the scene corresponding to the corresponding portions the captured initial images on the basis of the one of the corresponding portions of the captured initial images which has the determined highest image sharpness level.

This is advantageous because as the sharpness levels are different among RGB, this system can obtain the best sharpness values and provide this value to the other colour signals. This provides a higher quality resultant image. Also, this arrangement is easy to arrange using 3CMOS sensor systems.

4. The optical scope system according to clause 2, wherein:
   each of the image sensors is operable to capture light using a different respective one of red, green and blue (RGB) colour channels; and
   the image processor is operable to generate the portion of the captured image of the scene corresponding to the corresponding portions of the captured initial images by:
   transporting the image sharpness level of the one of the corresponding portions of the captured initial images which has the determined highest image sharpness level to the other corresponding portions of the captured initial images; and combining the one of the corresponding portions of the captured initial images which has the determined highest image sharpness level with the other corresponding portions of the captured initial images to which the determined highest image sharpness level has been transported.

5. The optical scope system according to any preceding clause, wherein each of the plurality of image sensors is located along a different respective optical path with respect to the lens arrangement.

This allows that the system to capture multiple differently focused images simultaneously.

6. The optical scope system according to any preceding clause, wherein the lens arrangement is operable to receive light from the scene captured by an optical instrument and to form the initial image of the scene on each image sensor using the received light, wherein the distance of each respective image sensor from the lens arrangement is determined on the basis of one or more characteristics of the optical instrument.

7. The optical scope system according to clause 6, comprising a plurality of image sensor adjustment devices (901A-901C) each operable to adjust the distance of a respective one of the image sensors from the lens arrangement.

This allows the distances between sensors and object to be adjustable.

8. The optical scope system according to clause 7, comprising:
   a user interface (912) operable to receive information from a user for determining the distance of each respective image sensor from the lens arrangement; and
   a controller (902) operable to control the image sensor adjustment devices to adjust the distance of each respective image sensor from the lens arrangement on the basis the received information.

9. The optical scope system according to clause 7, comprising:
   an instrument interface (122) operable to receive information from the optical instrument for determining the distance of each respective image sensor from the lens arrangement; and
   a controller (902) operable to control the image sensor adjustment devices to adjust the distance of each respective image sensor from the lens arrangement on the basis the received information.

10. The optical scope system according to clause 8 or 9, wherein the information for determining the distance of each respective image sensor from the lens arrangement comprises (a) the distance of each respective image sensor from the lens arrangement, (b) one or more optical properties of the optical instrument on the basis of which the controller is configured to calculate the distance of each respective image sensor from the lens arrangement, or (c) an identifier of the optical instrument on the basis of which the controller is configured to consult a database in order to obtain the distance of each respective image sensor from the lens arrangement or the one or more optical properties of the optical instrument for calculating the distance of each respective image sensor from the lens arrangement.

11. The optical scope system according to any one of clauses 6 to 10, wherein the optical instrument is an endoscope.

12. The optical scope system according to clause 11, wherein the endoscope is a medical endoscope.

This is particularly advantageous because in the field of medical endoscopy, the requirement for high resolution images with a long depth of field is high.

13. An endoscopic system comprising an optical scope system according to any one of clauses 6 to 10 and an optical instrument configured to capture light from the scene for use by the lens arrangement of the optical device in forming an initial image of the scene on each image sensor of the optical device.

14. A method of capturing an image of a scene in an optical scope system, the method comprising:
   capturing a plurality of initial images of the scene, each initial image of the scene being captured using a respective one of a plurality of image sensors, wherein each image sensor is located at a different respective distance from a lens arrangement operable to receive light from the scene and to form each initial image on each respective image sensor; and
   generating the captured image of the scene on the basis of image data from one or more of the captured initial images.

15. A recording medium storing a computer program for controlling a computer to perform a method according to clause 14.

16. An optical scope system (800) for capturing an image of a scene, the optical device comprising:
   means operable to capture a respective initial image of the scene;
   means operable to receive light from the scene and to form each initial image on each respective image sensor, each image sensor being located at a different respective distance from the lens arrangement; and
   means operable to generate the captured image of the scene on the basis of image data from one or more of the captured initial images.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

The invention claimed is:

1. An optical scope system for capturing an image of a scene, the optical scope system comprising:
a plurality of image sensors each operable to capture a respective initial image of the scene, each of the image sensors is operable to capture light using a different respective one of red, green and blue (RGB) color channels; and
at least one lens to receive light from the scene and to form each initial image on each respective image sensor, each image sensor being located at a different respective distance from the at least one lens; and
an image processor operable to:
divide each of the captured initial images into predetermined portions;
determine an image sharpness level for corresponding predetermined portions of each of the captured initial images;
determine the highest one of the determined image sharpness levels; and
generate, on the basis of image data from each of the captured initial images, the captured image of the scene so that a portion of the captured image of the scene corresponding to the corresponding predetermined portions of each of the captured initial images has a sharpness level equal to the determined highest image sharpness level, including
transporting the image sharpness level of the one of the corresponding predetermined portions of the captured initial images which has the determined highest image sharpness level to the other corresponding predetermined portions of the captured initial images; and
combining the one of the corresponding predetermined portions of the captured initial images which has the determined highest image sharpness level with the other corresponding predetermined portions of the captured initial images to which the determined highest image sharpness level has been transported.

2. The optical scope system according to claim 1, wherein each of the plurality of image sensors is located along a different respective optical path with respect to the at least one lens.

3. The optical scope system according to claim 1, herein the at least one lens receives light from the scene captured by an optical instrument and to form the initial image of the scene on each image sensor using the received light, wherein the distance of each respective image sensor from the at least one lens is determined on the basis of one or more characteristics of the optical instrument.

4. The optical scope system according to claim 3, comprising a plurality of image sensor adjustment devices each operable to adjust the distance of a respective one of the image sensors from the at least one lens.

5. The optical scope system according to claim 4, comprising:
a user interface operable to receive information from a user for determining the distance of each respective image sensor from the at least one lens; and
a controller operable to control the image sensor adjustment devices to adjust the distance of each respective image sensor from the at least one lens on the basis the received information.

6. The optical scope system according to claim 4, comprising:
an instrument interface operable to receive information from the optical instrument for determining the distance of each respective image sensor from the at least one lens; and
a controller operable to control the image sensor adjustment devices to adjust the distance of each respective image sensor from the at least one lens on the basis the received information.

7. The optical scope system according to claim 6, wherein the information for determining the distance of each respective image sensor from the at least one lens comprises (a) the distance of each respective image sensor from the at least one lens, (b) one or more optical properties of the optical instrument on the basis of which the controller is configured to calculate the distance of each respective image sensor from the at least one lens, or (c) an identifier of the optical instrument on the basis of which the controller is configured to consult a database in order to obtain the distance of each respective image sensor from the at least one lens or the one or more optical properties of the optical instrument for calculating the distance of each respective image sensor from the at least one lens.

8. The optical scope system according to claim 3, wherein the optical instrument is an endoscope.

9. The optical scope system according to claim 8, wherein the endoscope is a medical endoscope.

10. An endoscopic system comprising an optical scope system according to claim 3 and an optical instrument configured to capture light from the scene for use by the at least one lens of the optical instrument in forming an initial image of the scene on each image sensor of the optical instrument.

11. A method of capturing an image of a scene in an optical scope system, the method comprising:
capturing a plurality of initial images of the scene, each initial image of the scene being captured using a respective one of a plurality of image sensors, wherein each image sensor is located at a different respective distance from at least one lens to receive light from the scene and to form each initial image on each respective image sensor, each of the image sensors is operable to capture light using a different respective one of red, green and blue (RGB) color channels r;
dividing each of the captured initial images into predetermined portions;
determine an image sharpness level for corresponding predetermined portions of each of the captured initial images;
determining the highest one of the determined image sharpness levels; and
generating, on the basis of image data from each of the captured initial images, the captured image of the scene so that a portion of the captured image of the scene corresponding to the corresponding predetermined portions of each of the captured initial images has a sharpness level equal to the determined highest image sharpness level generating including transporting the image sharpness level of the one of the corresponding predetermined portions of the captured initial images which has the determined highest image sharpness level to the other corresponding predetermined portions of the captured initial images; and combining the one of the corresponding predetermined portions of the captured initial images which has the determined highest image sharpness level with the other corresponding predetermined portions of the captured initial images to which the determined highest image sharpness level has been transported.

12. A non-transitory recording medium storing a computer program for controlling a computer to perform a method according to claim 11.

13. An optical scope system for capturing an image of a scene comprising circuitry configured to perform a method according to claim 11.

* * * * *

UNITED STATES PATENT AND TRADEMARK OFFICE
CERTIFICATE OF CORRECTION

PATENT NO. : 11,146,723 B2
APPLICATION NO. : 16/464688
DATED : October 12, 2021
INVENTOR(S) : Thimo Emmerich et al.

Page 1 of 1

It is certified that error appears in the above-identified patent and that said Letters Patent is hereby corrected as shown below:

In the Claims

Column 12, Line 55 Claim 11:
Please delete "r" after channels.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*